United States Patent [19]
Jenkins et al.

[11] Patent Number: 5,591,434
[45] Date of Patent: Jan. 7, 1997

[54] DNA SEQUENCE ENCODING SURFACE PROTEIN OF CRYPTOSPORIDIUM PARVUM

[75] Inventors: Mark C. Jenkins, Bowie; Ronald Fayer, Ellicott City, both of Md.; Michael Tilley; Steven L. Upton, both of Manhattan, Kans.

[73] Assignees: The United States of America as represented by the Secretary of Agriculture, Washington, D.C.; Kansas State University Research Foundation, Manhattan, Kans.

[21] Appl. No.: 229,393

[22] Filed: Apr. 15, 1994

Related U.S. Application Data

[63] Continuation-in-part of Ser. No. 68,396, May 26, 1993, abandoned.

[51] Int. Cl.$^6$ ............ A61K 39/002; A61K 39/395; C07K 14/44; C07K 16/20; C12N 15/30; C12N 1/21; C12P 21/02; C12P 21/08

[52] U.S. Cl. ............ 424/191.1; 424/151.1; 424/265.1; 424/266.1; 435/69.3; 435/252.3; 435/252.33; 435/320.1; 530/350; 530/387.9; 530/395; 536/23.5; 536/23.7

[58] Field of Search ............ 536/23.7, 23.5; 530/350, 395, 387.9; 435/69.3, 252.3, 252.33, 320.1; 424/265.1, 266.1, 191.1, 151.1

[56] References Cited

U.S. PATENT DOCUMENTS

| | | | |
|---|---|---|---|
| 4,692,403 | 9/1987 | Lindner et al. | 435/5 |
| 4,849,329 | 7/1989 | Leung et al. | 435/2 |
| 5,028,694 | 7/1991 | Mewman et al. | 530/350 |
| 5,106,618 | 4/1992 | Beck et al. | 424/157.1 |
| 5,229,279 | 7/1993 | Peoples et al. | 435/135 |

FOREIGN PATENT DOCUMENTS

WO9324649 12/1993 WIPO.

OTHER PUBLICATIONS

Kumar et al. PNAS 87:1337–1340 1990.
Bowie et al. Science 247:1306–1310 1990.
Young et al. PNAS 80:1194–1198 1983.
Reperant et al. FEMS Microbiology Letters 99:7–14 Nov. 1992.
Smith et al. Mol. Cell Biology 3(12):2156–2165 1983.
Pennock et al. Mol Cell Biology 4(3):399–406 1984.
Tizard, I. (Editor) "An Introduction to Veterinary Immunology" 2nd Edition, published by W. B. Saunders Co. 1982 (Philadelphia, Penn.) see pp. 182–188.
Petersen, Carolyn, et al., "Identification and Initial Characterization of Five *Cryptosporidium parvum* Sporozoite Antigen Genes", *Infection and Immunity*, Jun. 1992, vol. 60, No. 6, pp. 2343–2348.
Tilley, Michael, et al. "Identification of a 15-Kilodalton Surface Glycoprotein on Sporozoites of *Cryptosporidium parvum*", *Infection and Immunity*, vol. 59, No. 3, pp. 1002–1007.

Riggs, Michael W., et al., "Neutralization-Sensitive Epitopes are Exposed on the Surface of Infectious *Cryptosporidium parvum* Sporozoites", *The Journal of Immunology*, vol. 13, No. 4, Aug. 15, 1989, pp. 1340–1345.

Tilley, Michael, et al., "*Cryptosporidium parvum* (Apicomplexa: Cryptosporidiidae) Oocyst and Sporozoite Antigens Recognized by Bovine Colostral Antibodies", *Infection and Immunity*, Sep. 1990, vol. 58 No. 9, pp. 2966–2971.

Kim, Kami, et al., "Isolation, Sequence and Molecular Karyotype Analysis of the Actin Gene of *Cryptosporidium parvum*", *Molecular and Biochemical Parasitology*, 50(1192), pp. 105–114.

Nelson, Richard G., et al., "Identification and Isolation of *Cryptosporidium parvum* Genes Encoding Microtubule and Microfilament Proteins", *Journal of Protozoology*, vol. 38, No. 6, Nov.–Dec. 1991, pp. 52S–55S.

Jenkins, M. C., et al., "Molecular cloning and Characterization of cDNA Encoding a 15 kDA *Cryptosporidium parvum* Surface Protein", The American Society of Parasitologists 67th Annual Meeting Program and Abstracts, The Univ. of Pennsylvania, Philadelphia, PA, Aug. 4–8, 1992.

Fayer, R., et al., "Hyperimmune Bovine Colostrum Neutralizes *Cryptosporidium* Sporozoites and Protects Mice Against Oocyst Challenge", *The Journal of Parasitology*, vol. 75, No. 1, Feb. 1989, pp. 151–153.

Fayer, R., et al., "Efficacy of Hyperimmune Bovine Colostrum for Prophylaxis of Cryptosporidiosis in Neonatal Calves", *The Journal of Parasitologists*, vol. 75, No. 3, Jun. 1989, pp. 393–397.

Laxer, Marc A., et al., "DNA Sequences for the Specific Detection of *Cryptosporidium parvum* by the Polymerase Chain Reaction", *Am. J. Trop. Med. Hyg.*, 45(6), 1991, pp. 688–694.

Gooze, Lisa, et al., "Amplification of a *Cryptosporidium parvum* Gene Fragment Encodign Thymidylate Synthase", *J. Protozool.*, vol. 38, No. 6, Nov.–Dec., 1991, pp. 56S–58S.

Fayer, R., "Immunogold Labeling of States of *Cryptosporidium parvum* Recognized by Immunoglobins in Hyperimmune Bovine Colostrum", *J. Parasitol*, 77(3) 1991, pp. 487–490.

*Primary Examiner*—Anthony C. Caputa
*Attorney, Agent, or Firm*—M. Howard Silverstein; Randall E. Deck; John D. Fado

[57] ABSTRACT

Recombinant proteins have been developed for the immunization of animals against cryptosporidiosis. The Proteins are effective for the immunization of a variety of animals against *Cryptosporidium parvum*, particularly for the production of hyperimmune colostrum that may be used to confer passive immunity against the parasite. Isolated DNA sequences which encode these proteins have also been developed. The DNA sequences may be inserted into recombinant DNA molecules such as cloning vectors or expression vectors for the transformation of cells and the production of the proteins.

17 Claims, 4 Drawing Sheets

FIG 1

| | |
|---|---|
| GCA CGA GTA TTG ATA AAA GAA AAA CAA AAC ATG GGT AAC TTG AAA TCC<br>Ala Arg Val Leu Ile Lys Glu Lys Gln Asn Met Gly Asn Leu Lys Ser<br>1               5                       10                  15 | 48 |
| TGT TGT TCT TTT GCC GAT GAA CAC TCC CTA ACC TCT ACT CAA CTA GTA<br>Cys Cys Ser Phe Ala Asp Glu His Ser Leu Thr Ser Thr Gln Leu Val<br>                 20                    25                    30 | 96 |
| GTT GGA AAT GGT TCA GGA GCT TCA GAA ACT GCT TCC AAC CAC CCC CAA<br>Val Gly Asn Gly Ser Gly Ala Ser Glu Thr Ala Ser Asn His Pro Gln<br>                35                    40                    45 | 144 |
| GAA GAA GTT AAT GAT ATC AAT ACT TTT AAT GTA AAG TTA ATA ATG CAA<br>Glu Glu Val Asn Asp Ile Asn Thr Phe Asn Val Lys Leu Ile Met Gln<br>    50                    55                    60 | 192 |
| GAT AGA AGT AAG CTT GAC TGC GAG GTA GTA TTT GAT AGC ACA AGT ATT<br>Asp Arg Ser Lys Leu Asp Cys Glu Val Val Phe Asp Ser Thr Ser Ile<br>65                    70                    75                  80 | 240 |
| TCG CTT TCT GGA GAT GGA AAA TGC AGA AAT ATT GCT TTG GAT GAA ATC<br>Ser Leu Ser Gly Asp Gly Lys Cys Arg Asn Ile Ala Leu Asp Glu Ile<br>                85                    90                    95 | 288 |
| CAC CAA TTA TTA TAT TCA AAG GAA GAG CTT TCT AGA GTT GAA AGT AGT<br>His Gln Leu Leu Tyr Ser Lys Glu Glu Leu Ser Arg Val Glu Ser Ser<br>          100                    105                110 | 336 |
| GCT GGA ATC AGC GAT TCC GAC AAT TGT GTT GCA ATT CAT CTC AAA GAA<br>Ala Gly Ile Ser Asp Ser Asp Asn Cys Val Ala Ile His Leu Lys Glu<br>          115                    120                125 | 384 |
| TCA GGA AAC TGT ATT CCC CTT TTC TTT AAT AAT TCG CAA GAC AAA GAA<br>Ser Gly Asn Cys Ile Pro Leu Phe Phe Asn Asn Ser Gln Asp Lys Glu<br>        130                    135                140 | 432 |
| AGA TTT GTT GCA ACA GCA AAC AAA TTC AAA CCA AAC TTT AAC<br>Arg Phe Val Ala Thr Ala Asn Lys Phe Lys Pro Asn Phe Asn<br>145                150                    155 | 474 |
| TAAAACAGGA ATTTCATTAA TTCTGGATTT GTTTTTTCCA AACCCTATAA ATAAAATCCA | 534 |
| AATAGCTTTT CTTCAATCAC AGGGAGAGAA TTAATAAAAT ATTTTTGATT AAAAAAAAAA | 594 |
| AAAAAAAA | 602 |

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 602 base pairs
        ( B ) TYPE: nucleic acid
        ( C ) STRANDEDNESS: double
        ( D ) TOPOLOGY: linear     ( i i ) MOLECULE TYPE: cDNA     ( i i i ) HYPOTHETICAL: NO     ( i v ) ANTI-SENSE: NO     ( v i ) ORIGINAL SOURCE:
        ( A ) ORGANISM: Cryptosporidium parvum
        ( D ) DEVELOPMENTAL STAGE: Sporozoite     ( v i i ) IMMEDIATE SOURCE:
        ( B ) CLONE: CP15/60

( i x ) FEATURE:
        ( A ) NAME/KEY: CDS
        ( B ) LOCATION: 1..474

( x i ) SEQUENCE DESCRIPTION: SEQ ID NO:1:

```
GCA  CGA  GTA  TTG  ATA  AAA  GAA  AAA  CAA  AAC  ATG  GGT  AAC  TTG  AAA  TCC        48
Ala  Arg  Val  Leu  Ile  Lys  Glu  Lys  Gln  Asn  Met  Gly  Asn  Leu  Lys  Ser
 1              5                        10                       15

TGT  TGT  TCT  TTT  GCC  GAT  GAA  CAC  TCC  CTA  ACC  TCT  ACT  CAA  CTA  GTA        96
Cys  Cys  Ser  Phe  Ala  Asp  Glu  His  Ser  Leu  Thr  Ser  Thr  Gln  Leu  Val
                 20                       25                       30

GTT  GGA  AAT  GGT  TCA  GGA  GCT  TCA  GAA  ACT  GCT  TCC  AAC  CAC  CCC  CAA       144
Val  Gly  Asn  Gly  Ser  Gly  Ala  Ser  Glu  Thr  Ala  Ser  Asn  His  Pro  Gln
             35                       40                       45
```

-continued

| | | | | | | | | | | | | | | | | |
|---|---|---|---|---|---|---|---|---|---|---|---|---|---|---|---|---|
| GAA | GAA | GTT | AAT | GAT | ATC | AAT | ACT | TTT | AAT | GTA | AAG | TTA | ATA | ATG | CAA | 192 |
| Glu | Glu | Val | Asn | Asp | Ile | Asn | Thr | Phe | Asn | Val | Lys | Leu | Ile | Met | Gln | |
| | 50 | | | | 55 | | | | | 60 | | | | | | |
| GAT | AGA | AGT | AAG | CTT | GAC | TGC | GAG | GTA | GTA | TTT | GAT | AGC | ACA | AGT | ATT | 240 |
| Asp | Arg | Ser | Lys | Leu | Asp | Cys | Glu | Val | Val | Phe | Asp | Ser | Thr | Ser | Ile | |
| 65 | | | | 70 | | | | | 75 | | | | | | 80 | |
| TCG | CTT | TCT | GGA | GAT | GGA | AAA | TGC | AGA | AAT | ATT | GCT | TTG | GAT | GAA | ATC | 288 |
| Ser | Leu | Ser | Gly | Asp | Gly | Lys | Cys | Arg | Asn | Ile | Ala | Leu | Asp | Glu | Ile | |
| | | | | 85 | | | | 90 | | | | | 95 | | | |
| CAC | CAA | TTA | TTA | TAT | TCA | AAG | GAA | GAG | CTT | TCT | AGA | GTT | GAA | AGT | AGT | 336 |
| His | Gln | Leu | Leu | Tyr | Ser | Lys | Glu | Glu | Leu | Ser | Arg | Val | Glu | Ser | Ser | |
| | | | 100 | | | | 105 | | | | | 110 | | | | |
| GCT | GGA | ATC | AGC | GAT | TCC | GAC | AAT | TGT | GTT | GCA | ATT | CAT | CTC | AAA | GAA | 384 |
| Ala | Gly | Ile | Ser | Asp | Ser | Asp | Asn | Cys | Val | Ala | Ile | His | Leu | Lys | Glu | |
| | | 115 | | | | 120 | | | | | 125 | | | | | |
| TCA | GGA | AAC | TGT | ATT | CCC | CTT | TTC | TTT | AAT | AAT | TCG | CAA | GAC | AAA | GAA | 432 |
| Ser | Gly | Asn | Cys | Ile | Pro | Leu | Phe | Phe | Asn | Asn | Ser | Gln | Asp | Lys | Glu | |
| | 130 | | | | 135 | | | | | 140 | | | | | | |
| AGA | TTT | GTT | GCA | ACA | GCA | AAC | AAA | TTC | AAA | CCA | AAC | TTT | AAC | | | 474 |
| Arg | Phe | Val | Ala | Thr | Ala | Asn | Lys | Phe | Lys | Pro | Asn | Phe | Asn | | | |
| 145 | | | | 150 | | | | | 155 | | | | | | | |

TAAAACAGGA ATTTCATTAA TTCTGGATTT GTTTTTCCA AACCCTATAA ATAAAATCCA  534

AATAGCTTTT CTTCAATCAC AGGGAGAGAA TTAATAAAAT ATTTTTGATT AAAAAAAAAA  594

AAAAAAAA  602

( 2 ) INFORMATION FOR SEQ ID NO:2:

( i ) SEQUENCE CHARACTERISTICS:
        ( A ) LENGTH: 158 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Ala Arg Val Leu Ile Lys Glu Lys Gln Asn Met Gly Asn Leu Lys Ser
 1               5                  10                  15
Cys Cys Ser Phe Ala Asp Glu His Ser Leu Thr Ser Thr Gln Leu Val
            20                  25                  30
Val Gly Asn Gly Ser Gly Ala Ser Glu Thr Ala Ser Asn His Pro Gln
        35                  40                  45
Glu Glu Val Asn Asp Ile Asn Thr Phe Asn Val Lys Leu Ile Met Gln
    50                  55                  60
Asp Arg Ser Lys Leu Asp Cys Glu Val Val Phe Asp Ser Thr Ser Ile
65                  70                  75                  80
Ser Leu Ser Gly Asp Gly Lys Cys Arg Asn Ile Ala Leu Asp Glu Ile
                85                  90                  95
His Gln Leu Leu Tyr Ser Lys Glu Glu Leu Ser Arg Val Glu Ser Ser
            100                 105                 110
Ala Gly Ile Ser Asp Ser Asp Asn Cys Val Ala Ile His Leu Lys Glu
        115                 120                 125
Ser Gly Asn Cys Ile Pro Leu Phe Phe Asn Asn Ser Gln Asp Lys Glu
    130                 135                 140
Arg Phe Val Ala Thr Ala Asn Lys Phe Lys Pro Asn Phe Asn
145                 150                 155
```

DNA SEQUENCE ENCODING SURFACE PROTEIN OF CRYPTOSPORIDIUM PARVUM

CROSS REFERENCE TO RELATED APPLICATION

This is a continuation-in-part of application Ser. No. 08/068,396, filed May 26, 1993, now abandoned.

BACKGROUND OF THE INVENTION

1. Field of the Invention

This invention relates to a novel protein for eliciting protective immune responses in animals against *Cryptosporidium parvum*, and recombinant DNA sequences which encode the protein.

2. Description of the Prior Art

The protozoan *Cryptosporidium parvum*, is spread by an oral-fecal route, infecting the intestinal epithelium and, to a lesser extent, the extraintestinal epithelia of a wide rare of mammalian species, causing severe diarrhea that can be life threatening. The young and immunosuppressed are at particularly high risk. Numerous reports of cryptosporidiosis in children attending day-care have been reported [Fayer and Ungar, Microbiol. Rev., 50(4):458–483, (1986)]. Although in most individuals the disease is self-limiting and protective immunity develops after a primary infection, cryptosporidiosis is a major cause of death in immunodeficient hosts such as persons afflicted with AIDS. As in humans, the young of animals are most susceptible to infection. Cryptosporidiosis is also a major disease of dairy and beef calves in the United States. At present, no prophylactic therapy is available to prevent this parasitic disease in humans or animals [Fayer and Ungar, ibid, and Dubey et al., Cryptosporidiosis in Man and Animals, CRC Press, Boca Raton, Fla. (1990)].

Several researchers have shown, however, that in calves, mice and humans, administration of hyperimmune bovine colostrum (HBC), prepared by immunizing cows with extracts of *C. parvum* oocysts, can effectively confer passive immunity against cryptosporidiosis [Fayer et al., J. Parasitol. 75(1):151–153 (1989); Fayer et al., J. Parasitol. 75(3):393–397 (1989); Fayer et al., Infect. Immun. 58(9):2962–2965 (1990); Nord et al., AIDS 4:581–584 (1990); Tzipori et al., Br. J. Med. 293:1276–1277 (1986); Tzipori et al., Lancet 2:244–245 (1987); and Ungar et al., Gastroenterology 98:486–489 (1990)]. Also, monoclonal antibodies and immune serum specific for *C. parvum* sporozoites can neutralize the parasite and either prevent or lessen the severity of infection in animals [Bjorneby et al., J. Immunol. 145(1):298–304 (1990); Bjorneby et al., Infect. Immnun. 59(3):1172–1176 (1991); Perryman et., Infect. Immun. 58(1):257–259 (1990); Riggs and Perryman, Infect. Immun. 55 (9):2081–2087 (1987); and Tilley et al., Infect. Immun. 59 (3):1002–1007 (1991)]. Although protection against *C. parvum* may be achieved by this type of immunotherapy, the development of resistance to cryptosporidiosis is dependent upon T lymphocytes and secreted lymphokines, in particular, gamma-interferon [Gardner, Am. J. Trop. Med. Hyg. 44(1):49–62 (1991); Mead et al., J. Infect. Dis. 163:1297–1304 (1991); McDonald et al., Infect. Immun. 60 (8):3325–3331 (1992); and Ungar et al., J. Immunol. 147 (3):1014–1022 (1991)]. The humoral response leading to production of protective antibodies specific for *C. parvum* may be dependent upon T cell signaling, but in persons with severe immunodeficiency T cell-mediated immunity is dysfunctional. Passive administration of hyperimmune serum or colostrum that is inhibitory for cryptosporidial parasites may be the only viable alternative for preventing or treating infection in such individuals.

SUMMARY OF THE INVENTION

We have now discovered a novel recombinant protein which is effective in the immunization of animals against cryptosporidiosis. The proteins are effective for the immunization of a variety of animals against *Cryptosporidium parvum*, particularly for the production of hyperimmune colostrum that may be used to confer passive immunity against the parasite. We have also discovered and isolated DNA sequences which encode these proteins. The DNA sequences may be inserted into DNA molecules such as cloning vectors or expression vectors for the transformation of cells and the production of the proteins.

It is an object of this invention to provide proteins, and the genes which encode them, that are effective for the immunization of animals against cryptosporidiosis.

It is also an object of this invention to provide recombinant DNA molecules containing the genes, for insertion into host cells and expression of the proteins.

Another object of the invention is to provide methods and compositions useful for protecting animals against cryptosporidiosis.

Other objects and advantages of this invention will become readily apparent from the ensuing description.

BRIEF DESCRIPTION OF THE DRAWINGS

FIG. 1. DNA sequence and predicted amino acid sequence of recombinant CP15/60 cDNA. (Coding sequence is shown 5' to 3', numerals to right of sequence reflect amino acid residue number.)

DEFINITIONS

The following terms are employed herein: Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transformed cells, e.g., tetracycline resistance or ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

DNA Coding Sequence. A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences and cDNA from eucaryotic mRNA. A polyadenylation signal and transcription termination sequence will usually be located 3' to the coding sequence.

DNA Sequence. A linear series of nucleotides connected one to the other by phosphodiester bonds between the 3' and 5' carbons of adjacent pentoses.

Expression. The process undergone by a structural gene to produce a polypeptide. Expression requires both transcription of DNA and translation of RNA.

Expression Vector. A replicon such as a plasmid, virus, retrovirus, bacteriophage, or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promoter and ribosome binding and interaction sequences.

Heterologous DNA. A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single stranded regions of nucleic acids to form double-stranded molecules.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Phage or Bacteriophage. Bacterial virus many of which include DNA sequences encapsidated in a protein envelope or coat ("capsid"). In a unicellular organism a phage may be introduced by a process called transfection.

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant."

Polypeptide. A linear series of amino acids connected one to the other by peptide bends between the alpha-amino and carboxy groups of adjacent amino acids.

Promoter. A DNA sequence within a larger DNA sequence defining a site to which RNA polymerase may bind and initiate transcription.

Reading Frame. The grouping of codons during translation of mRNA into amino acid sequences. During translation the proper reading frame must be maintained. For example, the DNA sequence may be translated via mRNA into three reading frames, each of which affords a different amino acid sequence.

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Replicon. Any genetic element (e.g., plasmid, chromosome, virus) that functions as an autonomous unit of DNA replication in vivo, i.e., capable of replication under its own control.

Start Codon. Also called the initiation codon, is the first mRNA triplet to be translated during protein or peptide synthesis and immediately precedes the structural gene being translated. The start codon is usually AUG, but may sometimes also be GUG.

Structural Gene. A DNA sequence which encodes through its template or messenger RNA (mRNA) a sequence of amino acids characteristic of a specific polypeptide.

Transform. To change in a heritable manner the characteristics of a host cell in response to DNA foreign to that cell. A cell has been introduced inside the cell wall. Exogenous DNA may or may not be integrated (covalently linked) to chromosomal DNA making up the genome of the cell. In procaryotes and yeast, for example, the exogenous DNA may be maintained on an episomal element such as a plasmid. With respect to eucaryotic cells, a stably transformed cell is one in which the exogenous DNA has been integrated into a chromosome so that it is inherited by daughter cells through chromosome replication. This stability is demonstrated by the ability of the eucaryotic cell to establish cell lines or clones comprised of a population of daughter cells containing the exogenous DNA.

Transcription. The process of producing mRNA from a structural gene.

Translation. The process of producing a polypeptide from mRNA.

DETAILED DESCRIPTION OF THE INVENTION

The present invention provides an isolated DNA sequence which encodes an antigenic protein effective for eliciting antibody production in an animal against *Cryptosporidium parvum*. The invention encompasses cDNA clones having a nucleotide sequence (SEQ ID No. 1) encoding rCP15/60 protein with the amino acid sequence of FIG. 1 (SEQ ID No. 2), as well as DNA sequences which encode proteins having amino acid sequences that are homologous to that of FIG. 1. "Homologous" proteins are defined herein as proteins having an amino acid sequence sufficiently duplicative of rCP15/60 protein to be antigenic and capable of eliciting antibody production against *C. parvum*. DNA sequences encoding rCP15/60 protein with the amino acid sequence shown in FIG. 1, and DNA sequences which encode homologous proteins and which also hybridize to the DNA sequence of FIG. 1 (or its complement) under stringent conditions are particularly preferred. The GenBank accession number of the nucleotide sequence shown in FIG. 1 is L3D8612.

Because of the degeneracy of the genetic code, there exists a finite set of nucleotide sequences which can code for a given amino acid sequence. It is understood that all such equivalent sequences are operable variants of the disclosed sequence, since all give rise to the same protein (i.e., the same amino acid sequence) during in vivo transcription and translation, and are hence encompassed by the instant invention. DNA sequences which are substantially homologous to the nucleotide sequence of FIG. 1 are also encompassed by the invention. As defined herein, two DNA sequences are substantially homologous when at least 85% (preferably at least 90% and most preferably 95%) of the nucleotides match over the defined length of the sequence. Sequences that are substantially homologous can be identified in a Southern hybridization experiment under stringent conditions as is known in the art. See, for example, Maniatis et al., Molecular Cloning: A Laboratory Manual, Cold Springs Harbor Laboratory, 1982, or DNA Cloning: A Practical Approach, Vol. I and II (Ed. D. N. Glover), IRL Press, Oxford, 1985.

The DNA sequences of the invention can be used to prepare recombinant DNA molecules by cloning in any suitable vector. A variety of vector-host combinations may be employed in practicing the present invention. Host cells may be either procaryotic or eucaryotic, and, when the host cells are bacterial cells, they may be either gram-negative or gram-positive bacteria. Without being limited thereto, useful hosts include *Escherichia coli*, species of Salmonella (including, for example, *S. typhimurium*, *S. enteriditis*, and *S. dublin*) species of Mycobacterium (such as *M. smegmatis* and *M. bovis*, species of Pseudomonas (including, for example, *P. aeruginosa* and *P. putida*), *Bacillus subtilis*, yeasts and other fungi (for example, *Saccharomyces cerevisiae*), plant cells such as plant cells in culture (including, for example, both angiosperms and gymnosperms) and animal cells such as animal cells in culture.

Vectors used in practicing the present invention are selected to be operable as cloning vectors or expression vectors in the selected host cell. Numerous vectors are known to those of skill in the art, and selection of an appropriate vector and host cell is a matter of choice. The vectors may, for example, he bacteriophage, plasmids, viruses, or hybrids thereof. A number of procaryotic expression vectors are described in U.S. Pat. Nos. 4,652,525, 4,440,859, 4,436,815, and 4,342,832, and a number of eucaryotic expression vectors have also been described in U.S. Pat. Nos. 4,546,082, 4,510,245, 4,446,235, and 4,443,540. Further, the vectors may he non-fusion vectors (i.e., those producing the antigenic protein of the invention not fused to any heterologous polypeptide), or alternatively, fusion vector (i.e., those producing the antigenic protein fused to a vector encoded polypeptide). The fusion proteins would of course vary with the particular vector chosen. Suitable non-fusion plasmid vectors for use with *E. coli* include but are not limited to pTrc99 for use with *E. coli* JM 105, or pANK-12, pANH-1 or pPL2 for use with *E. coli* MZ 1. Conversely, suitable fusion plasmid vectors include pGEX and pMC1871 for use with *E. coli* JM 105, pMAL with *E. coli* PR 722, pVB2 with *E. coli* LA5709, pTrcHis with *E. coli* INV F', pCO5 with *E. coli* N6405, and pRIT2T or pEZZ 18 with *E. coli* N4830-1. Other, non-*E. coli* expression systems which may also he employed include pAc360 or pBluescript for use with SP2 or High 5 insect cells, pYesHis with the yeast *C. cerevisiae* INVSc1 or INVSc2, pLS405 with *Salmonella dublin* SL598, and pYUB12 with *Mycobacterium smegmatis* or *M. bovis*. Still other suitable vector-host combinations that may be used in practicing the instant invention are described, for example, in U.S. Pat. No. 5,122,471, the contents of which are incorporated by reference herein.

Within each specific vector various sites may be selected for insertion of the isolated DNA sequence. These sites are usually designated by the restriction enzyme or endonuclease that cuts them. For example, in pBR322 the Pst I site is located in the gene for penicillinase between the nucleotide triplets that code for amino acids 181 and 182 of the penicillinase protein.

The particular site chosen for insertion of the selected DNA fragment into the vector to form a recombinant vector is determined by a variety of factors. These include size and structure of the polypeptide to be expressed, susceptibility of the desired polypeptide to enzymatic degradation by the host cell components and contamination by its proteins, expression characteristics such as the location of start and stop codons, and other factors recognized by those of skill in the art. None of these factors alone absolutely controls the choice of insertion site for a particular polypeptide. Rather, the site chosen reflects a balance of these factors, and not all sites may be equally effective for a given protein.

The DNA sequences of the invention may be inserted into the desired vector by known techniques. If, however, the vector is to serve as an expression vector, the vector should have a promoter, and the DNA sequence should be inserted in the vector downstream of the promoter and operationally associated therewith. While control sequences may be ligated to the coding sequence prior to insertion into the vector, preferably, the vector should be selected so as to have a promoter operable in the host cell into which the vector is to be inserted (that is, the promoter should be recognized by the RNA polymerase of the host cell). In addition, the vector should have a region which codes for a ribosome binding site positioned between the promoter and the site at which the DNA sequence is inserted so as to be operatively associated with the DNA sequence of the invention once inserted (in correct translational reading frame therewith). The vector should be selected to provide a region which codes for a ribosomal binding site recognized by the ribosomes of the host cell into which the vector is to be.

The antigenic proteins of the invention are produced by growing host cells transformed by the expression vectors described above under conditions whereby the antigen is produced. The antigens are then isolated from the host cells. The selection of the appropriate growth conditions and recovery methods are well within the skill of the art. The recombinant CP15/60 protein has been produced in a plurality of host vector systems, and its molecular weight has been determined to be about 17 kDa.

The present invention also encompasses methods to obtain isolated DNA sequences encoding the described antigenic proteins. In one embodiment, a DNA encoding the antigen may be prepared synthetically using standard techniques known in the art, as described, for example, in U.S. Pat. Nos. 5,112,575, 4,671,941, 4,598,049, 4,517,338, 4,483,964, or 4,353,989, the contents of each of which are incorporated by reference herein. Alternatively, another method is to construct a cDNA expression library using polyadenylated mRNA isolated from *C. parvum* sporozoites as described in Example 1 hereinbelow. The cDNA sequences are then inserted into DNA expression vectors to form recombinant vectors, and these are inserted into suitable host cells to form transformants expressing the DNA into protein. In one embodiment, the transformants producing the antigen may be identified by screening with antibody directed against *C. parvum* as described in the Example. However, it is preferred that the transformants be screened by Southern hybridization analysis using oligonucleotide probes capable of detecting a nucleotide sequence which encode the antigen.

Labeled oligonucleotide probes may be readily prepared using techniques known in the art, such as automated synthesis, using the nucleotide sequence encoding rCP15/60 disclosed herein. The particular nucleotide sequences selected are chosen so as to correspond to codons encoding an amino acid sequence of the antigen. While the exact length of the probe is not critical, is generally recognized that probes from about 15 to about 20 base pairs are usually effective. Greater selectivity may be achieved using longer probes. The probes may be labeled with a marker, such as a radionucleotide or biotin using standard procedures, and used to screen the libraries by Southern hybridization. Procedures for the hybridization assay are described, for example, in U.S. Pat. No. 5,041,378, and in Nucleic Acid Hybridization, (Ed. Hames and Higgins) 1985, the contents of each of which are incorporated by reference herein. Once a clone from the screened library has keen identified by positive hybridization, it can be confirmed by methods such as restriction enzyme analysis and DNA sequencing that the clone contains a gene that encodes the amino acid sequence of FIG. 1 or a homologous amino acid sequence.

The antigenic proteins of the present invention were used to immunize animals against *C. parvum*. While the proteins are effective for eliciting antibody production in a variety of animals, the proteins are particularly preferred for the treatment of bovine. The proteins may be administered to a target animal by any convenient route, such as subcutaneously, intraperitoneally, intramuscularly, or preferably intramammarily, in the presence of a physiologically acceptable diluent. The antigens may be administered in a single dose or in a plurality of doses, and may be administered, if desired, in combination with vaccine stabilizers and vaccine adjuvants. Typical stabilizers are, for example, sucrose, an alkali metal hydrogen phosphate salt, glutamate, serum albumin, gelatin, or casein. The stabilizer may be any one or more of the foregoing. The adjuvant may be, for example, alum or a composition containing a vegetable oil, isomannide monooleate and aluminum monostearate. The antigens of the present invention may be stored under refrigeration or in frozen or lyophilized form. The proteins are administered to the target animal in an amount effective to elicit a protective immune response against *C. parvum*, as compared to a control. The effective amount will vary with the particular target animal, its age and size, and may be readily determined by the practitioner skilled in the art.

In accordance with the preferred embodiment, the proteins are used to immunize bovine for the production of hyperimmune colostrum containing antibodies to *C. parvum* as described in Example 2. The hyperimmune colostrum so produced may be administered to target animals, particularly young or immunodeficient animals, to confer passive immunity against cryptosporidiosis. Without being limited thereto, the hyperimmune colostrum is particularly beneficial for the treatment of humans and bovine. Techniques for the production of hyperimmune colostrum and its use are known in the art and are described, for example Fayer et al., Nord et al., Tzipori et al., Ungar et al., referred to above.

While the protein may be administered to the target animal directly, it is also envisioned that the recombinant DNA containing an amino acid sequence encoding the protein could be administered to the animal as the immunizing agent. Suitable techniques for the treatment of animals with recombinant DNA are described, for example, by Tang et al., Nature 356:152–154 (1992), and Ulmer et al., Science 259:1745–1749 (1993), the contents of each of which are incorporated by reference herein.

Numerous issued U.S. patents are available which disclose information useful to those skilled in the art in practicing the present invention. U.S. Pat. No. 4,710,463 to Murray discloses recombinant DNA expression vectors incorporating DNA sequences coding for Hepatitis B virus antigens. U.S. Pat. No. 4,601,980 to Goeddel and Heyneker discloses the expression of a gene coding for human growth hormone in a pBR322/*E. coli* system. U. S. Pat. No. 4,590, 163 to Helinski and Ditta discloses RK2 plasmids useful for gene cloning in gram-negative bacteria such as *E. coli*. U.S. Pat. No. 4,237,224 to Cohen and Boyer discloses methods for producing recombinant DNA expression vectors. U.S. Pat. No. 4,332,897 to Nakano et al. discloses lambdoid bacteriophage vectors useful for transforming *E. coli*. U.S. Pat. No. 4,332,901 to Goldstein discloses a P4 derivative bacteriophage cloning vector. U.S. Pat. No. 4,704,362 to Itakura and Riggs and U.S. Pat. No. 4,356,270 to Itakura disclose recombinant plasmid vectors useful for transforming microbial hosts. U.S. Pat. No. 4,273,875 to Manis discloses a plasmid designated pUC6 useful as a cloning vector for transforming microbial hosts. U.S. Pat. No. 4,349, 629 to Carey et al. discloses plasmid vectors employing the trp bacterial promoter useful as recombinant DNA expression vectors. U.S. Pat. No. 4,362,817 to Reusser discloses the plasmid pUC1060, which contains a tet gene promoter, useful as an expression vector. U.S. Pat. No. 4,599,308 to Hamer et al. discloses SV40 expression vectors which can be introduced into eukaryotic cells. U.S. Pat. No. 4,693,976 to Schilperoort et al., U.S. Pat. No. 4,536,475 to Anderson, and 4,459,355 to Cello and Olsen all concern the transformation of plant cells with the Ti plasmid of *Agrobacterium* tumefaciens. The disclosures of all U.S. patent references cited herein are to be incorporated herein by reference.

The following examples are intended only to further illustrate the invention and are not intended to limit the scope of the invention as defined by the claims.

EXAMPLE 1

Preparation of parasite nucleic acid and protein. *Cryptosporidium parvum* oocysts ($2\times10^8$ per preparation) were recovered from feces of cows during days 4–14 of a severe cryptosporidial infection. Oocysts were concentrated by sucrose flotation followed by purification over a cesium chloride gradient using the procedures described by Tilley et al. [Infect. Immun., 59(3):1002–1007, (1991)]. After centrifugation, oocysts were resuspended in 5.0 ml of 10 mM Tris-HCl pH 8.0, 1 mM EDTA (TE) and immersed dropwise into a mortar containing a liquid nitrogen. The frozen parasites were ground in liquid nitrogen to a fine powder which was transferred to a tube containing the appropriate extraction buffer. Total *C. parvum* RNA was isolated by immersing the parasite extract in a mixture of guanidinium thiocyanate, sodium citrate, phenol and sodium acetate followed by centrifugation and ethanol precipitation using standard procedures as described by Xie and Rothblum [Biotechniques, 11 (3):324–327 (1991), the contents of which are incorporated by reference herein]. DNA of *C. parvum* was prepared by treating the parasite extract with 1% sodium dodecylsulfate (SDS) and 50 ug/ml proteinase K (Gibco/BRL, Gaithersburg, Md.) in TE at 50° C. for 2 h followed by phenol-chloroform extraction [Owen and Boorman, Nucl. Acid Res., 15(8):3631, (1987), the contents of which are incorporated by reference herein]. Oocyst protein was prepared by resuspending the parasite extract in 10 mM Tris-HCl pH 7.3, 1mM $MgCl_2$ in the presence of phenylmethylsulfonyl-fluoride (PMSF), sonicating for 20 sec at setting 10 (Heat Systems Inc., Farmingdale, N.Y.) and treating with 5 ug/ml DNase and RNase for 15 min on ice [Jenkins and Dame, Mol. Biochem. Parasitol., 25:155–164, (1987)].

Generation of polyclonal rat antisera.

Oocysts of *C. parvum* were purified on CsCl gradients [Taghi-Kilani and SeKal, Am. J. Trop. Med. Hyg., 36:505–508, (1987)] washed four times in PBS, freeze/thawed three times to release antigen. Proteins from $1.4\times10^9$ oocysts were separated using 12% SDS-PAGE. A small vertical strip of the gel was excised and stained with Coomasie blue for visualization purposes. The strip was realigned with the rest of the gel and a horizontal strip corresponding to the area of CP15 excised. CP15 was electroeluted from the gel using a BioRad model 422 ELECTROELUTER, dialyzed against distilled water overnight, and divided into 3 equal aliquots. One aliquot was emulsified in Freund's complete adjuvant and injected subcutaneously (SC) into a male Sprague-Dawley outbred rat (Harlan Sprague-Dawley). The second aliquot was mixed with Freund's incomplete adjuvant and injected SC 2 weeks later. The third aliquot was injected SC without adjuvant 2 weeks later. The rat was bled by heart puncture 4 days after the last injection. In accordance with approved animal procedures, the rat was anethesized during each immunization and the heart puncture.

Preparation and screening of C. parvum sporozoite cDNA bacteriophage expression libraries.

Poly A+RNA was isolated by passing 210 ug of total *C. parvum* RNA through an oligo dT spun column and used to prepare cDNA following procedures supplied by the manufacturer (Stratagene, La Jolla, Calif.). The resultant sporozoite cDNA was fractionated by gel filtration through a SEPHAROSE CL4B column (Pharmacia/LKB, Piscataway, N.J.) into two size categories-greater than 350 bp (CP1) and between 200 and 350 bp (CP2) and then introduced into the UNIZAP XR bacteriophage expression vector utilizing techniques provided by the manufacturer (Stratagene). Unamplified CP1 was compact of $2.4\times10_6$ phage particles and CP2 was composed of $2.1\times10^6$ phage particles; both contained greater than 95% recombinant clones. The libraries were amplified on *E. coli* XL1 Blue and immunoscreened for expression of recombinant CP15 antigen using the polyclonal rat sera prepared against native *C. parvum* 15 kDa protein, supra.

Immunoreactive UNIZAP XR bacteriophage expressing CP15 epitopes were made clonal by repeated rounds of screening with the anti-CP15 sera at bacteriophage densities that allowed single plaque isolation. An immunoreactive UNIZAP XR bacteriophage clone, designated CP15/60, was identified by screening about $10^6$ of the CP1 clones.

In vivo excision and DNA sequencing of *C. parvum* cDNA.

Recombinant PBLUESCRIPT plasmid DNA was generated and subjected to dideoxy sequencing. The recombinant PBLUESCRIPT plasmid containing *C. parvum* cDNA (CP15/60) was prepared using an in vivo excision protocol supplied by the manufacturer (Stratagene). Plasmid DNA was prepared [Wang et al., Biotechniques, 6(9):839–842, (1991)] and used to determine the DNA sequence of the insert cDNA employing SEQUENASE and reagents for dideoxy sequencing following techniques provided by the manufacturer (U.S. Biochemical, Cleveland, Ohio). The predicted amino acid sequence of the encoded recombinant protein was based on the reading frame of UNIZAP XR and the DNA sequence of the cDNA. Putative N-glycosylation sites (Asn-X-Ser or Asn-X-Thr) were identified by analysis using the Intelligenetics program (Intelligenetics, Inc., Mountain View, Calif.). Transmembrane regions and signal sequences were identified using standard techniques [Von Heinje, Biochem. Biophys. Acta, 947:307–333, (1988)].

Upon analysis, the insert cDNA was about 600 bp and had a long poly A tail (SEQ ID No. 1). The sequence of the cDNA and the corresponding predicted amino acid sequence of the encoded protein (SEQ ID No. 2) are shown in FIG. 1. The predicted amino acid sequence appeared to contain two N-linked glycosylation sites (residues 35–37 and 154–156), a signal sequence (residues 1–27), and a transmembrane region (residues 36–57).

Northern and Southern blot hybridization experts.

Total *C. parvum* sporozoite RNA (20 ug per lane) was subjected to formaldehyde gel electrophoresis [Sambrook et al., Molecular Cloning, Cold Spring Harbor Laboratory Press, Cold Spring Harbor, N.Y., (1989)] and transferred to NYTRAN paper (Scheicher and Schuell, Keene, N.H.). Sporozoite DNA of *C. parvum* (2 ug per lane) was digested with various restriction enzymes, fractionated by agarose electrophoresis, and transferred to NYTRAN paper [Southern, J. Mol. Biol., 98:503–517, (1975)]. An equimolar amount of insert cDNA relative to the estimated size of the *C. parvum* genome (about $6\times10^6$ bp, 11) was also electrophoresed and transferred to determine the copy number of the cloned gene fragment. Thus, 200 pg of insert DNA or 1.2 ng of restriction enzyme-dig plasmid DNA [$6\times10^6$ bp (size of insert) /$6\times10^6$ bp (size of *C. parvum* genome)×2 ug (amount of genomic EA electrophoresed in adjacent lanes)] was analyzed. Insert cDNA was isolated by double-digestion of recombinant PBLUESCRIPT plasmid DNA with EcoRI and XhoI (Gibco/BRL) and subsequent agarose electrophoresis. The insert cDNA was excised from the gel, isolated using the PREP-A-GENE kit following procedures supplied by the manufacturer (BioRad, Richmond, Calif.), and radiolabeled with $^{32}$P-dCTP using random oligomers and Klenow DNA polymerase using manufacturer's instructions (Gibco/ BRL). The cDNA probes were denatured by heating in a boiling water bath for 5 min, quick-chilled in an ice bath, and applied to both Southern and Northern blots that had been prehybridized as described [Jenkins et al., Exp. Parasitol., 66:96–107, (1988)]. After 24 h hybridization with radiolabeled cDNA, blots were once with 2×SSC, 0.1% SDS at room temperature followed by three washes in 0.2×SSC, 0.1% SDS at 50° C. After drying, blots were exposed to Kodak XAR film and stored at −70° C. until development.

Figure 2:
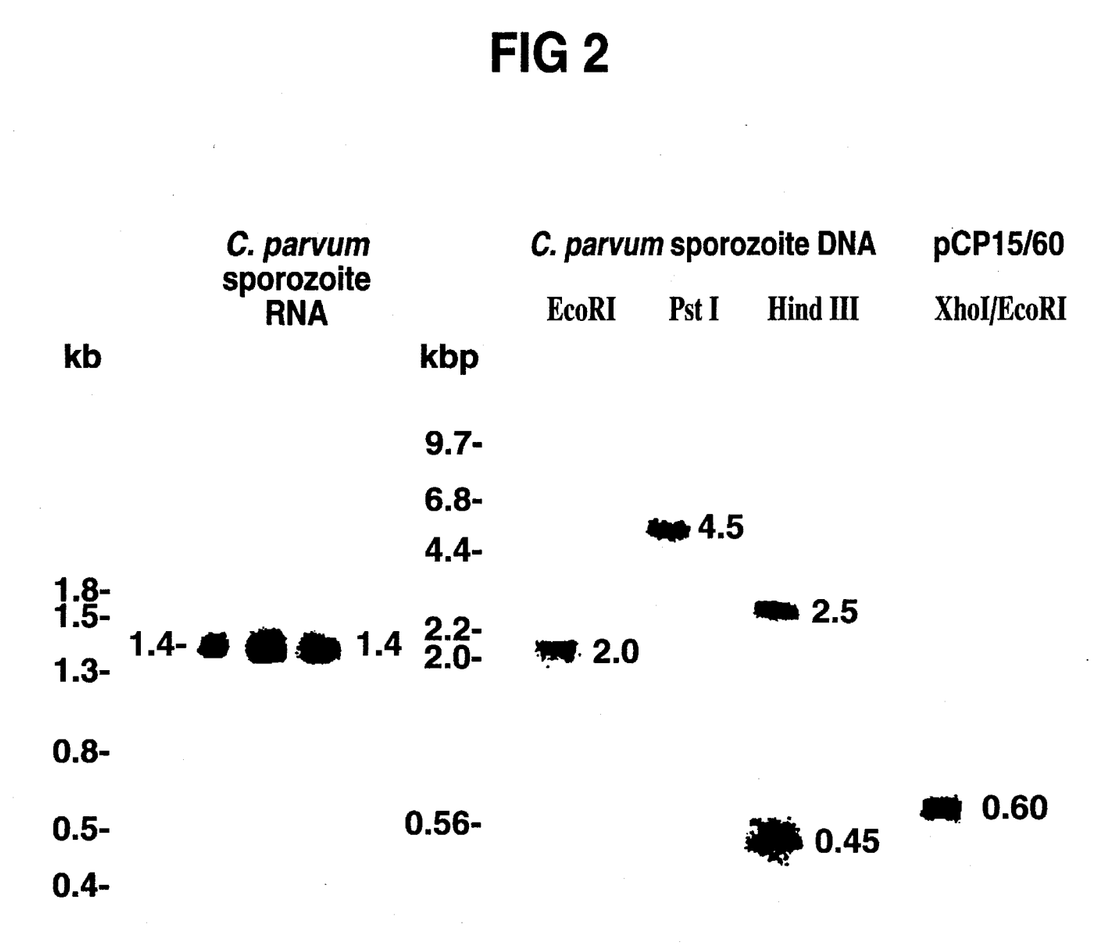
FIG. 2. Northern and Southern blot hybridization of CP15/60 cDNA to formaldehyde gel-separated *Cryptosporidium parvum* total RNA and 0.8% agarose gel-separated *C. parvum* genomic DNA. RNA samples derived from three separate nucleic acid extractions were compared. An equimolar amount of insert cDNA (relative to the amount of genomic DNA in adjacent lanes) was electrophoresed as XhoI/EcoRI digestion products of CP15/60 plasmid DNA. kb, RNA standards (BRL); kbp, DNA standard (HindIII-digested lambda DNA, BRL).

Hybridization of CP15/60 cDNA to Northern blots containing *C. parvum* total RNA revealed a 1.4 kb transcript (FIG. 2). The 1.4 kb RNA species was present in about equal concentrations from three separate oocyst extractions. Southern blot hybridization of CP15/60 to genomic DNA of *C. parvum* sporozoites showed single hybridizing bands in DNA digested with EcoRI and PstI and two bands in DNA digested with HindIII (FIG. 2). The latter result was not unexpected since the cDNA contains a single HindIII site. CP15/60 appears to be a single or low copy number gene since hybridization of the insert cDNA to equimolar amounts of CP15/60 and genomic DNA showed hybridizing bands of similar intensity.

High level expression of *C. parvum* cDNA in *E. coli* and analysis by Western blotting.

Insert cDNA was isolated by digesting recombinant PBLUESCRIPT plasmid DNA with beth BamHI and XhoI, subsequent agarose electrophoresis, excision from the gel and treatment with the PREP-A-GENE reagents (BioRad). Purified cDNA was subcloned into BamHI/XhoI-digested PTRCHIS (Invitrogen, San Diego, Calif.) using T4 DNA LIGASE (Gibco/BRL) and expressed in *E. coli* JM101 by isopropylthiogalactopyranoside (IPTG) induction using methods supplied by the manufacturer. After 4 h IPTG induction, *E. coli* harboring recombinant or non-recombinant PTRCHIS plasmid were harvested by centrifugation and resuspended in sonication buffer containing protease inhibitors (see above). The *E. coli* were subjected to three freeze-thaw cycles, sonication on ice for 20 sec, followed by DNase and RNase treatment. Expression of *C. parvum* cDNA was evaluated y SDS-PAGE followed by electrophoretic transfer to Immobilon paper (Millipore, Bedford, Mass.). Western blots containing recombinant and non-recombinant protein from uninduced and IPTG-induced *E. coli* were treated with phosphate buffered-saline containing and 1% non-fat dry milk (PBS-NFDM) for 1 h at room temperature (RT) to block non-specific binding in later steps. The protein-impregnated paper was the probed for 4–24 h at RT with either anti-CP15 immune serum or monoclonal antibody 5C3 to CP15 [Tilley et al., (1991), ibid] followed by a 2 h incubation with biotin-labeled anti-mouse IgG (0.5 mg/ml, Vector Laboratories, Burlingame, Calif.), followed by a 1 h incubation with avidin-peroxidase (0.25 m/ml, Vector Laboratories). The Western blots were washed three times with PBS containing 0.05% TWEEN 20 for 5 min per wash between each incubation step and developed by the addition of 0.5 mg/ml 4-chloro-1-naphthol and 0.015% H20substrate in PBS (Sigma Chemical Co., St. Louis, Mo.). Recognition of native and recombinant *C. parvum* proteins by immune serum and monoclonal antibody.

Figure 3:
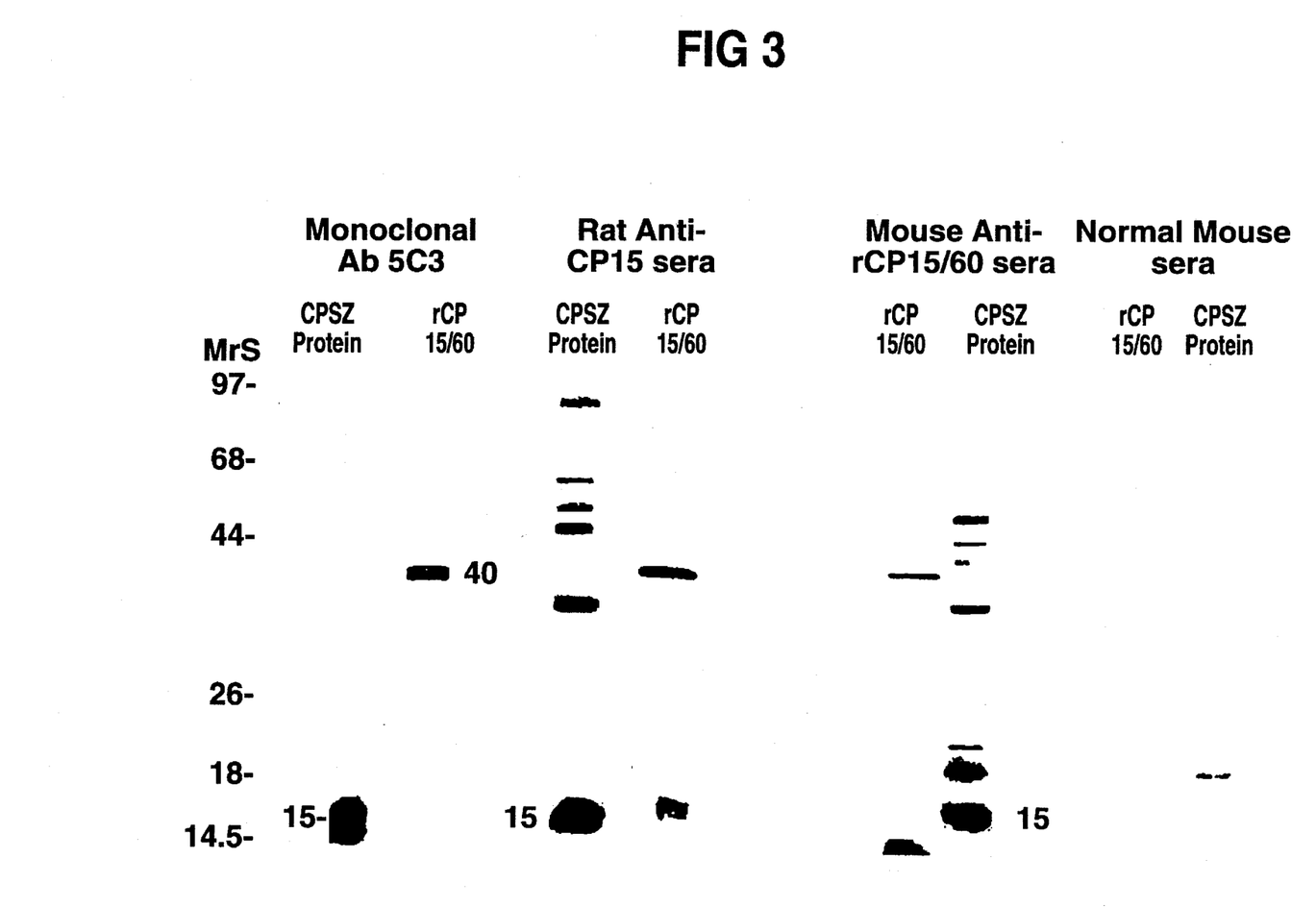
FIG. 3. Immunostaining of Western blots containing native *Cryptosporidium parvum* sporozoite protein and purified recombinant CP15/60 protein. The primary immunoreagents were either monoclonal antibody 5C3, rat anti-native CP15 sera normal mouse sera, or mouse anti-recombinant CP15/60 sera. MrS, molecular weight standards.

In immunoblotting experiments, rCP15/60 was recognized as a 40 kDa fusion protein by beth monoclonal antibody 5C3 (to CP15 protein) and rat anti-native CP15sera (FIG. 3). This fusion protein was about 18 kDa larger than expected based on the size of the open reading frame of CP15/60 (which would indicate a molecular weight of 17 kDa) and the peptide encoded by the parental plasmid (5 kDa). The unexpected size of the peptide was due to the nature of this particular vector.

Purification of recombinant CP15 protein.

Protein extracts from IPTG-induced *E. coli* containing either recombinant or non-recombinant plasmid were separated by preparative SDS-PAGE and transblotted to nitrocellulose membrane. Western blots were treated with PONCEAU S stain (Sigma) to visualize the recombinant protein which was then excised as a horizontal strip from the paper. A horizontal strip from an adjoining region of the Western blot containing non-recombinant protein was also excised. Both strips were cut into 0.5 cm pieces and placed in separate tubes containing 2.0% SDS and 1.0% TRITON-X 100 to elute the proteins from the paper. The eluted proteins were analyzed by SDS-PAGE followed by COOMASSIE BLUE staining or transblotting to nitrocellulose membrane and immunostaining with specific sera.

Antisera prepared in mice by immunization with purified rCP15/60 antigen bound epitopes of native *C. parvum* 15 and 60 kDa proteins (FIG. 3). Sera from mice immunized with non-recombinant *E. coli* protein bound neither antigen.

Immmofluorescence staining of parasites.

Sporozoites were obtained by excystation of purified *C. parvum* oocyst using standard methods [Riggs and Perryman, Infect. Immun., 55(9):2081–2087, (1987)]. Excysted sporozoites were washed several times in PBS and then either stored live on ice, air-dried onto glass slides, or treated for 5 min with 1% paraformaldehyde (PF). PF-treated parasites were washed several times with PBS, and then air-dried onto glass slides. Untreated live sporozoites, PF-treated, and air-dried parasites were incubated in PBS containing 1% bovine serum albumin (BSA) for 1 h at RT. After preincubation in PBS-BSA, the parasites were exposed for 1 h at 4° C. to a 1:100 dilution of mouse antiserum specific for purified recombinant CP15/60 protein in PBS-BSA-0.05% sodium azide. To prepare immune sera, three mice received two intraperitoneal injections of purified recombinant CP protein in incomplete Freund's adjuvant (see above). Sera from mice immunized with non-recombinant *E. coli* protein were used as negative controls. After incubation with mouse antisera, the *C. parvum* sporozoites were washed three times in PBS, treated for 1 h with fluorescein-isothiocyanate conjugated goat anti-mouse IgG (Sigma), followed by three additional PBS washes. The slides were then examined under epifluorescence to visualize the antibody binding pattern.

Antisera prepared against rCP15/60 bound an antigen on the surface of live *C. parvum* sporozoites. This antigen appeared to be distributed unevenly on the sporozoite surface. IFA staining of paraformaldehyde-treated or dried sporozoites showed that the antigen was also a component of internal structures at the apical end of the parasite.

EXAMPLE 2

Immmunization of cows for production of colostral anti-rCP15/60 antibodies.

Recombinant CP15/60 and control protein purified as described above were emulsified 1:1 in Freund's Incomplete Adjuvant and used to immunize separate cows by intramuscular injection 8 weeks before parturition. The cows received intramammary injections of a similar antigen preparation at 6 and 4 weeks before parturition. The primary immunization consisted of 0.25 mg recombinant CP15/60 protein (or an equivalent amount of control protein). The second and third immunizations consisted of 0.25 mg protein injected into the left front and left rear quarters and 0.1 mg protein injected into the right front and right rear quarters. After parturition, the cows were milked twice daily for 3 days and colostrum was prepared using standard procedures. The antibody response to recombinant CP15/60 and control antigen was assessed by enzyme-linked immunosorbent assay (ELISA) and immunoblotting as described below.

Determination of colostral antibody titers to recombinant CP15/60 and control protein by enzyme-linked immmosorbent assay.

Protein extracts from IPTG-induced *E. coli* harboring either recombinant CP15/60 plasmid or non-recombinant plasmid were prepared as described above and then treated with 3M urea to solubilize protein. Total protein concentration in the urea-soluble extracts was estimated using the BCA assay (Pierce Chemical Co. ). Urea-soluble recombinant CP15/60 and control protein was diluted in 0.1M carbonate buffer, pH 9.5 and pipetted into individual wells of IMMUNOLON II microtiter plates at 1.0 ug per well and stored overnight at 4° C. to allow binding of antigen to the plate surface. Unbound antigen was removed by washing the microtiter plates with phosphate-buffered saline containing 0.5% TWEEN 20 (PBS-TW20). The wells were treated with PBS-TW20 containing 5% horse serum for 1 h at room temperature (RT) to block non-specific antibody bind in subsequent steps. Colostrum from cows immunized with recombinant or control antigen was added to separate wells in serial ten-fold dilutions in PBS-TW20 for 2 h at RT, followed by rabbit anti-bovine IgG,A,M for 2 h at RT and then phosphatase-labeled sheep anti-rabbit IgG for 2 h at RT.

The wells were washed three times between each incubation step with PBS-TW20. Antibody binding was assessed by incubation with substrate for 30 min. at RT and reading on a microtiter plate reader (Dynatech) at 450 nm. Titers of anti-recombinant CP15/60 immunoglobulin were determined as the reciprocal of the highest serum dilution in wells containing rCP15/60 that produced an $O.D._{450}$ two standard deviations greater than the mean $O.D._{450}$ reading in wells containing control antigen.

Immunostaining of Western blots containing recombinant and control antigen with immune colostrum was performed to ensure that ELISA readings reflected anti-rCP15/60 responses. The SDS-PAGE and Western blotting procedure was identical to that described above.

Figure 4:
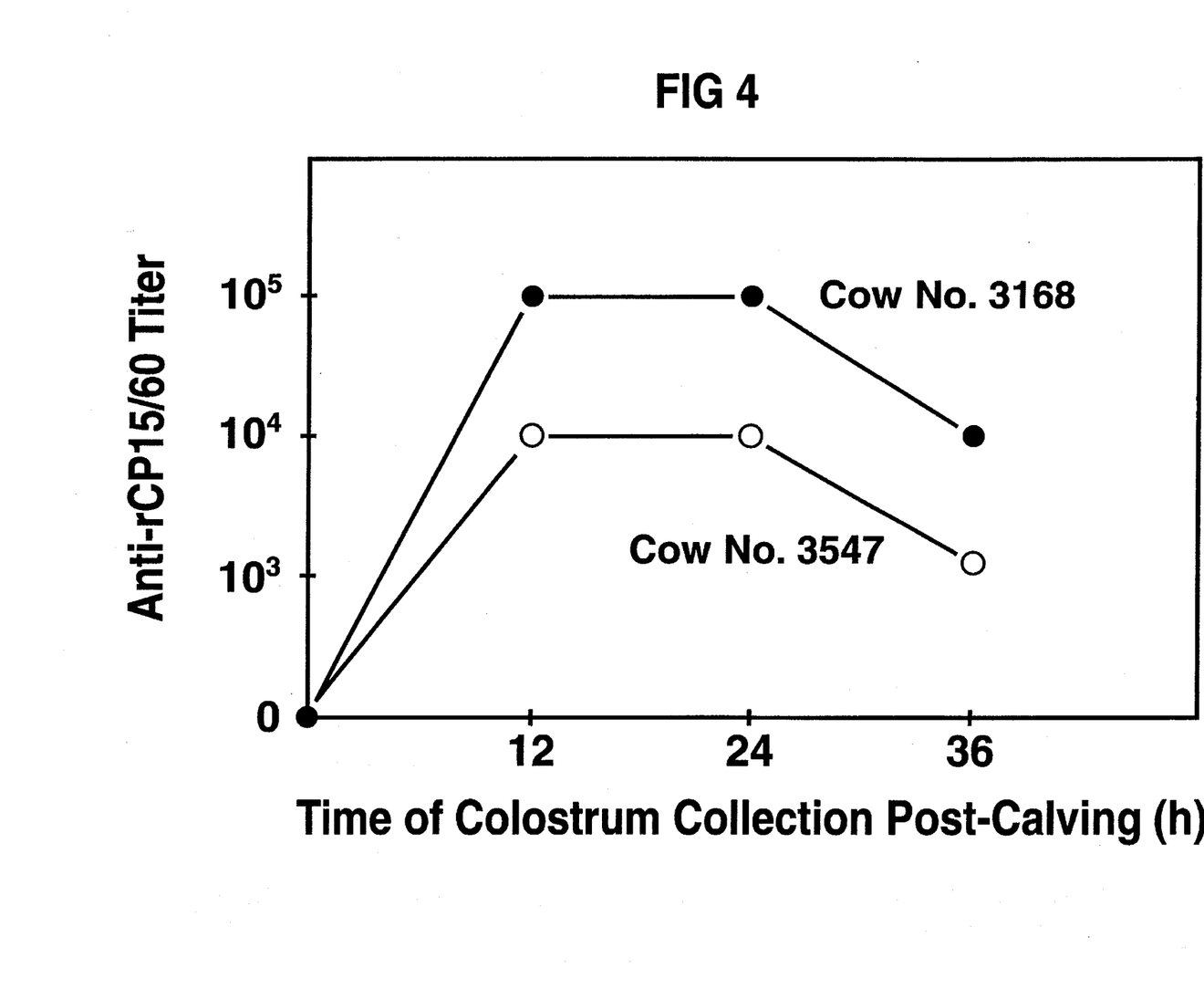
FIG. 4. Antibody titers to recombinant CP15/60 in colostrum from cows immunized by intramuscular and intramammery injection of rCP15/60 as indicated by enzyme-linked immunosorbent assay.

Cows immunized with recombinant CP15/60 antigen exhibited high colostral immunoglobulin titers against rCP15/60 (FIG. 4). Cow no. 3168 showed titers between $10^4$ and $10^5$ at the 1st and 2nd milking which decreased to between $10^3$ and $10^5$ at 3rd milking. Cow no. 3547 showed titers greater than $10^5$ at the 1st and 2nd milking which decreased to between $10^4$ and $10^5$ at the 3rd milking. As shown by immunoblotting, colostrum from cows no. 3168 and 3547 recognized recombinant CP15/60 antigen.

It is understood that the foregoing detailed description is given merely by way of illustration and that modifications and variations may be made therein without departing from the spirit and scope of the invention.

We claim:

1. An isolated DNA molecule consisting of the nucleotide sequence encoding rCP15/60 protein consisting of the amino acid sequence of amino acids 1 through 158 of SEQ ID No.

2, wherein said protein is antigenic and effective to elicit an immune response against *Cryptosporidium parvum* in a host animal.

2. The DNA molecule of claim 1 wherein said molecule is a cDNA molecule encoding rCP15/60 protein.

3. The DNA molecule of claim 1 consisting of the nucleotide sequence of nucleotides 1 through 474 of SEQ ID No. 1.

4. A recombinant DNA molecule comprising the DNA molecule of claim 1 inserted therein.

5. A recombinant DNA molecule comprising the DNA molecule of claim 3 inserted therein.

6. A recombinant DNA comprising a expression vector having a promoter and a nucleotide sequence of claim 1 downstream of said promoter and operatively associated therewith.

7. The recombinant DNA of claim 6 wherein said recombinant DNA molecule is selected from the group consisting of a plasmid, bacteriophage, phage, and virus.

8. A transformed host cell comprising the recombinant DNA of claim 6, and wherein said transformed host cell is effective for the production of said protein.

9. The transformed host cell of claim 8 wherein said host cell is a eucaryotic cell.

10. The transformed host cell of claim 8 wherein said host cell is a procaryotic cell.

11. The transformed host cell of claim 10 wherein said procaryotic cell is *Escherichia coli*.

12. An isolated protein comprising the amino acid sequence of amino acids 1 through 158 of SEQ ID No. 2.

13. A composition comprising the isolated protein of claim 12 and a pharmaceutically acceptable carrier.

14. A method for protecting an animal against *Cryptosporidium parvum* comprising administering the isolated protein of claim 12 to said animal in an amount effective to elicit an immune response against *Cryptosporidium parvum* therein.

15. A method for producing hyperimmune colostrum containing antibodies to *Cryptosporidium parvum* comprising:

(a) administering the isolated protein of claim 12 to an animal in an amount effective to elicit an immune response against *Cryptosporidium parvum* therein;

(b) collecting hyperimmune colostrum containing antibodies specifics for *Cryptosporidium parvum* from said animal.

16. A method as described in claim 15 wherein said animal is a cow.

17. A method for protecting an animal against *Cryptosporidium parvum* comprising administering said hyperimmune colostrum of claim 15 to an animal.

\* \* \* \* \*